United States Patent
Aurora et al.

(10) Patent No.: US 9,144,599 B2
(45) Date of Patent: Sep. 29, 2015

(54) SUPPRESSION OF BONE LOSS BY INTRODUCING FOXP3+ CD8 T-CELLS ($TC_{REG}$)

(71) Applicant: Saint Louis University, St. Louis, MO (US)

(72) Inventors: Rajeev Aurora, Wildwood, MO (US); Zachary Buchwald, St. Louis, MO (US); Jennifer Kiesel, Pacific, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 14/043,412

(22) Filed: Oct. 1, 2013

(65) Prior Publication Data

US 2014/0093475 A1 Apr. 3, 2014

Related U.S. Application Data

(60) Provisional application No. 61/708,447, filed on Oct. 1, 2012.

(51) Int. Cl.
*A61K 35/17* (2015.01)
*A61K 38/19* (2006.01)
*A61K 38/17* (2006.01)

(52) U.S. Cl.
CPC .............. *A61K 38/191* (2013.01); *A61K 38/178* (2013.01); *A61K 35/17* (2013.01)

(58) Field of Classification Search
CPC ............................ A61K 38/191; A61K 35/17
See application file for complete search history.

(56) References Cited

PUBLICATIONS

Kiesel et al., J Immunol 2009; 182:5477-5487.*

\* cited by examiner

*Primary Examiner* — Daniel C Gamett
(74) *Attorney, Agent, or Firm* — Lewis Rice LLC

(57) ABSTRACT

Systems and methods for inhibiting bone loss using FoxP3+ CD8 T-cells ($Tc_{REG}$). Osteoclasts are induced to produce FoxP3+ CD8 T-cells ($Tc_{REG}$) either in vivo or ex vivo. The FoxP3+ CD8 T-cells ($Tc_{REG}$) are provided to the patient to subsequently regulate osteoclast function, thereby establishing a bi-directional regulatory loop between osteoclasts and FoxP3+ CD8 T-cells ($Tc_{REG}$).

1 Claim, 9 Drawing Sheets

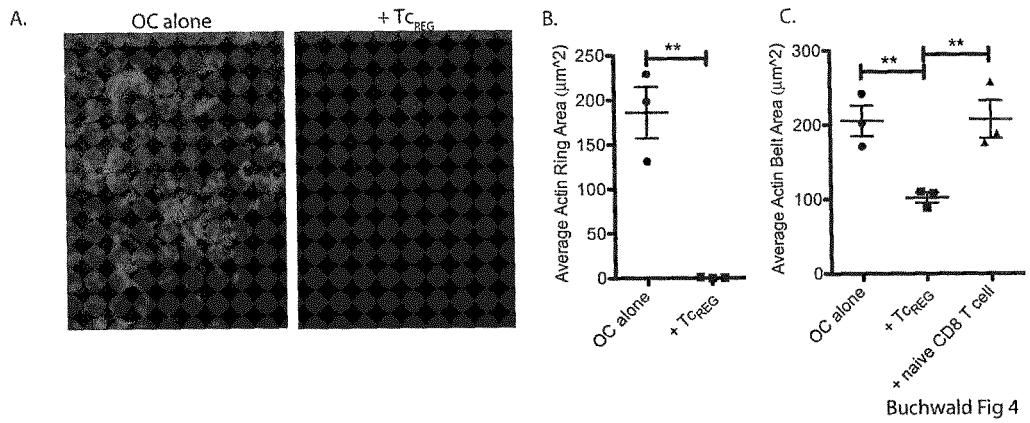

Buchwald Fig 4

Tc$_{REG}$ suppress mature osteoclasts by effecting the cytoskeletal reorganization: Osteoclasts were cultured either alone or with Tc$_{REG}$ on bovine bone chips for 24 hrs. T-cells were then removed, and osteoclasts were stained with phalloidin-Texas Red to visualize actin rings. Representative images are shown in panel A. Quantitation of three independent experiments is shown in panel B. Panel C is quantitation of phalloidin staining of osteoclasts plated on tissue culture treated dishes. Statistical significance of actin ring area was assessed by non-parametric paired T test: **: $P<0.01$ in comparison to osteoclast alone.
doi:10.1371/journal.pone.0038199.g004

FIG. 3

SUPPRESSION OF BONE LOSS BY INTRODUCING FOXP3+ CD8 T-CELLS (TC$_{REG}$)

CROSS REFERENCE TO RELATED APPLICATION(S)

This application claims the benefit of U.S. Provisional Patent Application Ser. No. 61/708,447, filed Oct. 1, 2012, the entire disclosure of which is herein incorporated by reference.

BACKGROUND OF THE INVENTION

1. Field of the Invention

This disclosure is related to the field of devices, methods, treatments and processes for suppressing bone loss and inflammation in individuals. Specifically, this disclosure relates to exploitation of the bi-directional regulatory loop between osteoclasts and FoxP3+ CD8 T-cells through cell-based therapies, biologics, small molecule agonists, or other known methodologies to suppress bone loss, control inflammatory responses and/or illicit certain desired responses from the human immunological and/or skeletal systems.

2. Description of Related Art

The human skeletal system is a dynamic system—an individual's bone structure is constantly being remodeled. Bone consists of a protein matrix embedded in a mineral layer. Two cells play a key role in the ever-changing reconstruction of an individual's bone structure throughout his or her life: osteoclasts and osteoblasts. Osteoclasts are large multinucleated cells that are the principal, if not sole, bone resorbing cells in the body. Stated differently, and simply, osteoclasts are cells that remove bone tissue from the skeletal system through bone resorption; i.e., by removing and breaking up a bone's mineralized matrix. Osteoblasts, which are the cells responsible for bone formation, balance the function of osteoclasts. The activity of osteoblasts is regulated by several growth factors, including transforming growth factor beta and bone morphogenetic protein. Osteoblasts, in turn, regulate the production of osteoclasts by secreting macrophage colony stimulating factor (M-CSF) and displaying the receptor activator of NF-κB ligand (RANKL) on their cell surface to induce cells of the monocytic/macrophage lineage to develop into osteoclasts.

In healthy organisms, the two cells operate in homeostasis with the amount of bone resorption, and formation, being in harmony. Alteration of the carefully balanced roles of osteoclasts and osteoblasts in this dynamic system can result in the creation of certain problematic conditions. For example, increased activity of osteoblasts, but more commonly the decreased activity of osteoclasts, leads to osteopetrosis, where the bones become overly dense leading to stress fractures. In contrast, increased activity of osteoclasts or decreased activity of osteoblasts, leads to bone deconstruction which can manifest itself in osteoporosis and Paget's disease, which result in bones being fragile and brittle.

Recently it has been discovered that the equilibrium of the skeletal system, skeletal homeostasis, does not operate in a vacuum but, rather, is dynamically influenced by the human immune system. For example, lymphocyte-derived cytokines, such as the receptor activator of NF-κB ligand (RANKL), interleukin (IL)-17 and type I and II interferons, are potent mediators of osteoclast function and osteoclastogenesis. Further, osteoclast activity and numbers are increased by cytokines produced by pro-inflammatory effector T-cells, augmentation of which leads to the bone erosion which occurs in inflammatory diseases such as rheumatoid arthritis and periodontitis. T-cell produced cytokines also play a critical role in bone cancers, post-menopausal osteoporosis, and in Paget's disease. This crosstalk between the immune and skeletal system has been termed osteoimmunology.

Currently, one way in which inflammation and bone-loss-based diseases, such as but not limited to osteoporosis, rheumatoid arthritis, periodontitis, Paget's disease and bone cancers, are treated is through multiple classes of anti-inflammatory agents including nonsteroidal anti-inflammatory agents/analgesics (NSAIDs), steroids and biologics that mediate the TNFα blockade. These forms of treatment address the effects of the disease; i.e., reducing inflammation, but do not directly counteract the underlying bone loss. Generally, these forms of treatment are effective in about 30-50% of patients. However, each of these classes of anti-inflammatory agents also have severe safety and adverse reaction issues, which tend to limit their use in specific populations.

Another treatment methodology for inflammatory and bone-loss-based diseases are drugs or biologics which directly treat osteoporosis and bone erosion. For example, bisphosphonates (also called diphosphonates) are a widely-prescribed class of drugs that prevent the loss of bone mass by inhibiting the digestion of bone though encouraging osteoclasts to undergo apoptosis, or cell death, thereby slowing bone loss. However, use of bisphosphonates comes with serious safety issues. First, osteonecrosis of the jaw is increased in patients taking bisphosphonates. Second, even though bisphosphonates slow bone loss, the risk of bone fracture in elderly patients is increased in patients on this class of drugs. This increase is most likely due to the fact that suppression of bone remodeling by bisphosphonates leads to an effete skeletal structure since bone remodeling (both the removal of old bone and new bone formation) is required to keep bone strength. As bisphosphonates are irreversible inhibitors, the removal of old bone in this carefully balanced system is suppressed, placing a patient at additional risk for a fracture.

Other biologics which directly treat osteoporosis and bone erosion include Denosumab, a fully human monoclonal antibody designed to block the effect of RANKL and possibly TNFα. However, higher incidences of infection have been reported in patients treated with Denosumab, possibly because of the off-target effect on TNFα. Another biologic is pulsed parathyroid hormone (PTH), a treatment which has been demonstrated to decrease bone fractures and increase bone density in postmenopausal osteoporosis. PTH targets osteoblasts to increase bone function and has shown great promise in the treatment of osteoporosis. However, the high cost of PTH (currently about $40,000 per year) has limited its use. Notably, neither PTH nor Denosumab have any noted effect of decreasing inflammation.

SUMMARY OF THE INVENTION

Because of these and other problems in the art, described herein, among other things, is a cell-based therapy using FoxP3+ CD8 T-cells (Tc$_{REG}$). Osteoclasts are induced to produce FoxP3+ CD8 T-cells or they can be supplied ex vivo. Once induced, the FoxP3+ CD8 T-cells subsequently regulate osteoclast function, thereby establishing a bi-directional regulatory loop between osteoclasts and FoxP3+ CD8 T-cells. This bi-directional regulatory loop evidences a previously unknown crosstalk between the skeletal and immune system which can be exploited through cell-based therapeutics, biologics, small molecule agonists or other known methodologies to treat bone-loss and inflammation-based diseases. It is also contemplated that the bi-directional regulatory loop may be exploited to facilitate desired immune responses; e.g., to overcome certain mechanisms used to evade immune surveillance by cancerous cells.

There is described herein, among other things, a method for reducing bone loss in a patient, the method comprising: generating osteoclasts from ex vivo blood of the patient by culturing blood mononuclear cells with M-CSF and RANKL; generating T-cells from the ex vivo blood; isolating the osteoclasts and the T-cells from the ex vivo blood; generating ex vivo the patient, FoxP3+ CD8 T-cells ($Tc_{REG}$); and introducing the ($Tc_{REG}$) to the patient.

There is also described herein, a method for reducing bone loss in a patient, the method comprising: generating FoxP3+ CD8 T-cells ($Tc_{REG}$) by providing blood from the patient with an inducer through the use of immobilized antibodies, the inducer selected from the group consisting of: Notch ligand, MHC-I+Ag, and CD200; introducing the ($Tc_{REG}$) to the patient.

In an embodiment of the method, the blood from the patient is ex vivo the patient during the generating.

In an embodiment of the method, the blood from the patient is in vivo the patient during the generating.

There is also described herein is a method for reducing bone loss in a patient, the method comprising: providing the patient a RANK agonist being of: sufficient amount to induce osteoclasts of the patient to produce FoxP3+ CD8 T-cells ($Tc_{REG}$); and insufficient amount to activate enough of the osteoclasts to create bone loss in the patient; wherein, the RANK agonist activates a negative feedback loop through the $Tc_{REG}$.

In an embodiment of the method, the RANK agonist is RANKL.

In an embodiment of the method, RANKL is provided in a low dose of about 0.125 mg/kg or less.

BRIEF DESCRIPTION OF THE DRAWINGS

FIG. 3A-C depict the experimental results that demonstrate that $Tc_{REG}$ can directly suppress mature osteoclasts by affecting their cytoskeletal reorganization.

DESCRIPTION OF THE PREFERRED EMBODIMENT(S)

Figure 1:
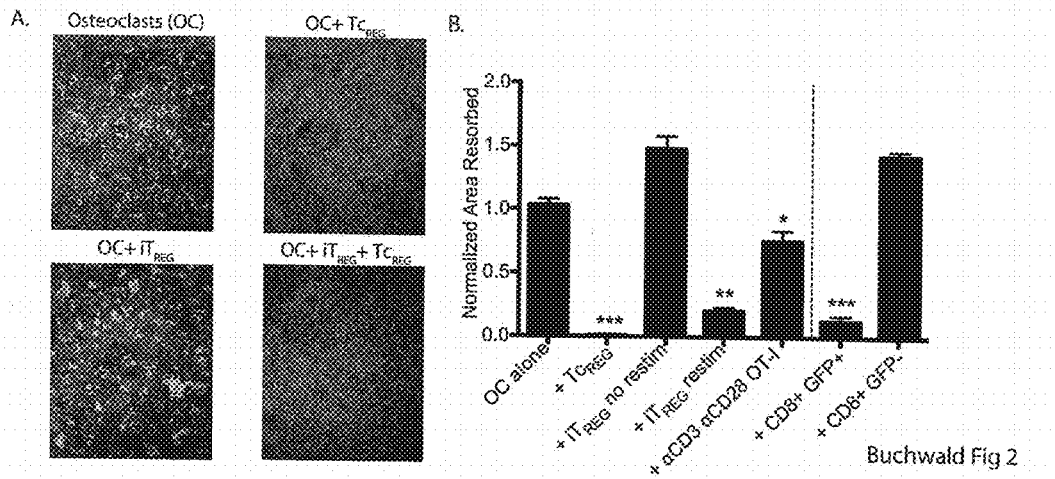
FIGS. 1A and B depict the experimental results that demonstrate that osteoclast-induced FoxP3+ CD8 T-cells ($Tc_{REG}$) secreted cytokines could potently and directly suppress resorption by osteoclasts.

In general, the immune system which dynamically influences skeletal homeostasis and osteoclast and osteoblast activity, also maintains two counterbalancing cell types: effectors and regulatory T-cells. Effectors (e.g., TH17), which are dominant during the inflammatory phase, regulate pathways by increasing or decreasing the pathway's reaction rate. Regulatory T-cells (TREG), are a subpopulation of T-cells which modulate the immune system, maintain tolerance to self-antigens, suppress the aberrant activation of self-reactive T-cells, and abrogate autoimmune disease. TREG mediate their regulatory function through a number of mechanisms. First, TREG express anti-inflammatory cytokines including IL-10, TGFβ, and IL-35. Another mechanism of regulation is by cell-to-cell contact: cytotoxic T-lymphocyte antigen-4 (CTLA-4) expressed on TREG binds with ~10 fold higher affinity to co-stimulatory B7 molecules on antigen presenting cells (APC) than CD28, and thus prevent APC from activating naïve T-cells. TREG have also been proposed to prevent differentiation of effector T-cells by consuming cytokines (IL-2, IL-4 and IL-7) required for T-cell activation and polarization.

The transcription factor FoxP3 is a marker of TREG that have the ability to suppress aberrant activation of self-reactive T-cells. TREG cells that express FoxP3 also express CD25, the α-chain of the IL-2 receptor. Under non-inflammatory conditions, osteoclasts can recruit naïve CD8 T-cells and activate these T-cells to induce CD25 and Fox P3, as demonstrated in Kiesel, et al., Cross-presentation by osteoclasts induces FoxP3 in CD8+ T-cells, J. Immunology, 182:5477-5487 (2009), the entire disclose of which is incorporated herein by reference. Thus, osteoclasts can act as APC.

For example, osteoclasts can endocytose exogenous proteins and process the proteins into peptides to present them to CD8 T-cells. This ability to present exogenous antigens on MHC class I is unexpected because this property has, until now, only been found in the so-called "professional" APC, such as dendritic cells; it is an unusual property/activity for a non-immune cell, such as an osteoclast, to have. The osteoclast-induced CD8-T-cells which express FoxP3 and CD25 do not have cytolytic activity, are anergic (i.e., they do not proliferate or respond to antigen on second exposure), and they can suppress the proliferation of naïve CD8 T-cells. A general overview of this process, along with some description from the present disclosure, can be found in Buchwald, et al., Osteoclasts and CD8 T Cells Form a Negative Feedback Loop That Contributes to Homeostasis of Both the Skeletal and Immune Systems, Clinical and Developmental Immunology, 2013:429373 (2013), the entire disclose of which is incorporated herein by reference.

As described more fully below in the provided Examples, through examination and experimentation, it was discovered that osteoclast-induced FoxP3+ CD8 T-cells ($Tc_{REG}$), whether produced in situ (e.g., produced by co-culture), ex vivo or in vivo (e.g., isolated from an organism) could control osteoclast activity and suppress bone resorption. This ability of osteoclasts to induce $Tc_{REG}$ and the ability of $Tc_{REG}$ to subsequently regulate osteoclast function, establishes a bi-directional regulatory loop between osteoclasts and $Tc_{REG}$ cells in bone marrow. This bi-directional regulatory loop generally consists of three steps, as demonstrated in FIG. 9: (a) induction of FoxP3 by osteoclasts in CD8 T-cells (101), creating FoxP3+ CD8 T-cells; (b) regulation of naïve T-cell priming by osteoclast-induced FoxP3+ CD8 T-cells (102); and (c) suppression of osteoclasts by osteoclast-induced FoxP3+ CD8 T-cells (103).

This bi-directional regulatory loop suggests a new physiological role for $Tc_{REG}$ than was previously understood—the inhibition of osteoclast activity under homeostatic conditions. $Tc_{REG}$ cells can suppress osteoclast resorptive function and thus provide a novel control function for regulatory T-cells beyond regulation of the immune system. The ability of osteoclasts to induce $Tc_{REG}$ and the ability of $Tc_{REG}$ to subsequently regulate osteoclast function establishes a negative feedback loop between these two cells in the bone marrow. Thus, these results evidence a previously unknown crosstalk between the skeletal and immune system which is profoundly connected on two levels. First, the immune system can not only activate the skeletal system by pro-inflammatory cytokines, but also negatively regulate it to maintain or restore homeostasis. Second, the results evidence that osteoclasts are antigen-presenting cells that induce FoxP3 to produce novel regulatory CD8 T-cells that can regulate both the skeletal and immune systems. Further, the $Tc_{REG}$ not only limit bone resorption, but also have the ability to modulate the immune system by decreasing the number of effector T-cells. Thus, $Tc_{REG}$ have the ability to inhibit osteoclast activity and treat inflammatory responses resulting from effector T-cells regardless of form of introduction.

Figure 9:
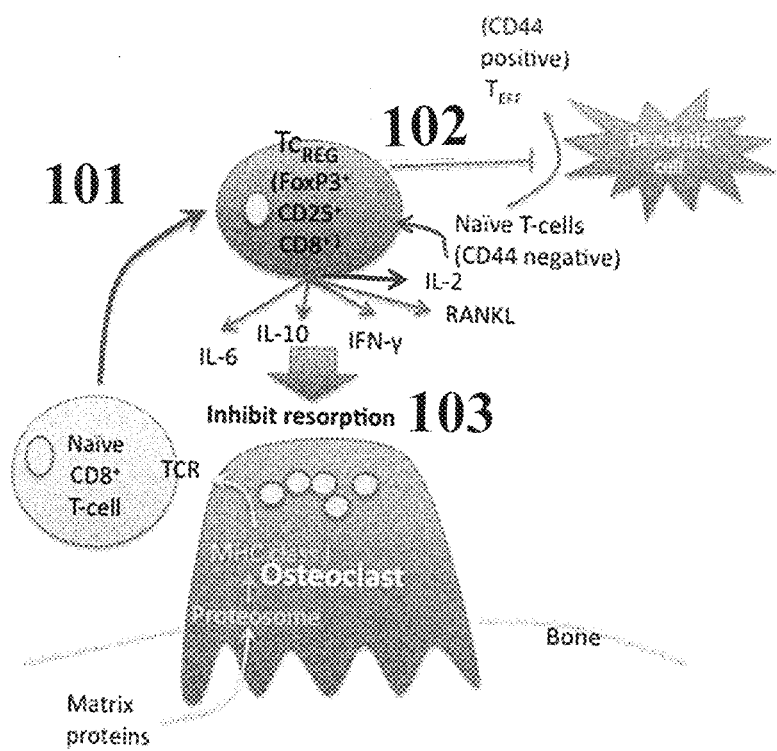
FIG. 9 depicts the bi-directional regulatory loop between osteoclasts and FoxP3+ CD8 T-cells described herein.

This physiological role of $Tc_{REG}$ can be exploited in a number of ways to modulate osteoclast activity, inflammatory responses of the immune system and maintain homeostasis of the skeletal system. It is contemplated that any step in this bi-directional regulatory loop can be exploited. For example, as depicted in FIG. 9, induction of FoxP3 by osteoclasts in CD8 T-cells can be stimulated (101); naïve T-cell priming can be regulated by osteoclast-induced $Tc_{REG}$ (102); or osteoclasts can be suppressed by osteoclast-induced $Tc_{REG}$ (103).

One contemplated treatment methodology is cell-based therapy. As described further herein, FoxP3 CD8 T-cells can be generated in vivo, in vitro and ex vivo. It is contemplated that these cells, whether produced in vivo, in vitro and ex vivo, can be reintroduced into a patient as a therapy in order to exploit the bi-directional regulatory loop to suppress osteoclast activity, restore homeostasis and/or control inflammatory responses. For example, osteoclasts can be generated from human peripheral blood by culturing blood mononuclear cells with M-CSF and RANKL (two cytokine factors). T-cells can be isolated from the blood as well. Using theses osteoclasts and T-cells, $Tc_{REG}$ can be generated from a patient's blood ex vivo and then reintroduced as a cell-based therapy.

Another option for cell-based therapy is to induce $Tc_{REG}$ in the absence of osteoclasts by exploiting the three signal pathways, i.e., Notch ligand, MHC-I+Ag and CD200, that osteoclasts utilize to induce $Tc_{REG}$. By using immobilized antibodies, the immunological synapse formed between osteoclasts and the T-cells to induce $Tc_{REG}$ can be activated without osteoclasts. It is contemplated that these signal pathways can be activated both in vivo or ex vivo.

Another contemplated treatment methodology is induction of $Tc_{REG}$ through the administration of a biologic or small molecule agonist into a patient. For example, because RANKL has been found to induce $Tc_{REG}$, a biologic or small molecule RANK agonist could be used to induce $Tc_{REG}$ and thereby suppress bone loss and control inflammatory conditions. Although RANKL promotes bone loss by activating osteoclasts, low dose RANKL which in an embodiment comprises about 0.125 mg/kg or less suppresses bone loss by activating a negative feedback loop through $Tc_{REG}$. Thus, drugs could be developed that promote osteoclasts to induce $Tc_{REG}$ or could act on CD8 T-cells to induce $Tc_{REG}$. In addition, biologics or small molecule agonists that activate the pathways in naïve CD8 T-cells that osteoclasts utilize to induce $Tc_{REG}$; i.e., Notch ligand, MHC-I+Ag and CD200, could also be used to induce $Tc_{REG}$.

Amongst other treatment possibilities, it is contemplated that the above-described methodologies can be utilized to suppress bone loss in postmenopausal osteoporosis, rheumatoid arthritis, periodontitis and other bone-loss associated diseases. Another treatment possibility is the suppression of bone loss and pathological fractures when certain tumors (e.g., breast and prostate tumors) metastasize to the bone.

In addition to treating bone-loss-based diseases through suppression of bone loss, it is contemplated that the above-described methodologies can be utilized to control and treat inflammatory responses.

It is also contemplated that the above-described methodologies could be utilized to manipulate and alter the body's immunological response to tumors and cancers present in the body. For example, surveillance of the immune system keeps tumors in check by mounting an immunological response to these altered cells. One of the mechanisms used by cancer cells to evade immune surveillance is the induction of regulatory T-cells which, in-turn, suppress the organism's natural immune responses. It is contemplated that, by inactivating $Tc_{REG}$ through the pathways utilized by osteoclasts to induce $Tc_{REG}$; i.e., Notch ligand, MHC-I+Ag and CD200, this suppression of the immune system could be averted and the immune system would be able to mount a response to destroy primary and metastasized tumors.

The above-described treatments can be used to treat both bone-loss and inflammation-based diseases. These treatments are advantageous over the currently utilized methodologies for inflammation and bone-loss-based diseases for a number of reasons. First, unlike many of the currently utilized treatments, $Tc_{REG}$ can target both bone loss and inflammation. Further, because $Tc_{REG}$ can be generated from a patient's own blood, the adverse effects of this approach are likely to be minimal. Further, the ability to generate $Tc_{REG}$ in a patient by low dose RANKL or potentially through a drug that mimics RANKL (such as a RANKL agonist) in the bone or at the site of bone erosion is likely to have significant benefits because it limits bone loss and decreases the inflammation that is driving bone erosion. Finally, the ability to induce $Tc_{REG}$ in situ at the site of inflammation and bone erosion should increase the safety and efficacy of these therapeutic treatments.

The below-described Examples describe certain examination and experimentation which demonstrate that osteoclast-induced FoxP3+ CD8 T-cells ($Tc_{REG}$), whether produced in situ (e.g., produced by co-culture), ex vivo or in vivo (e.g., isolated from an organism), can control osteoclast activity and suppress bone resorption.

Example 1

In Vitro Assays

Figure 2:
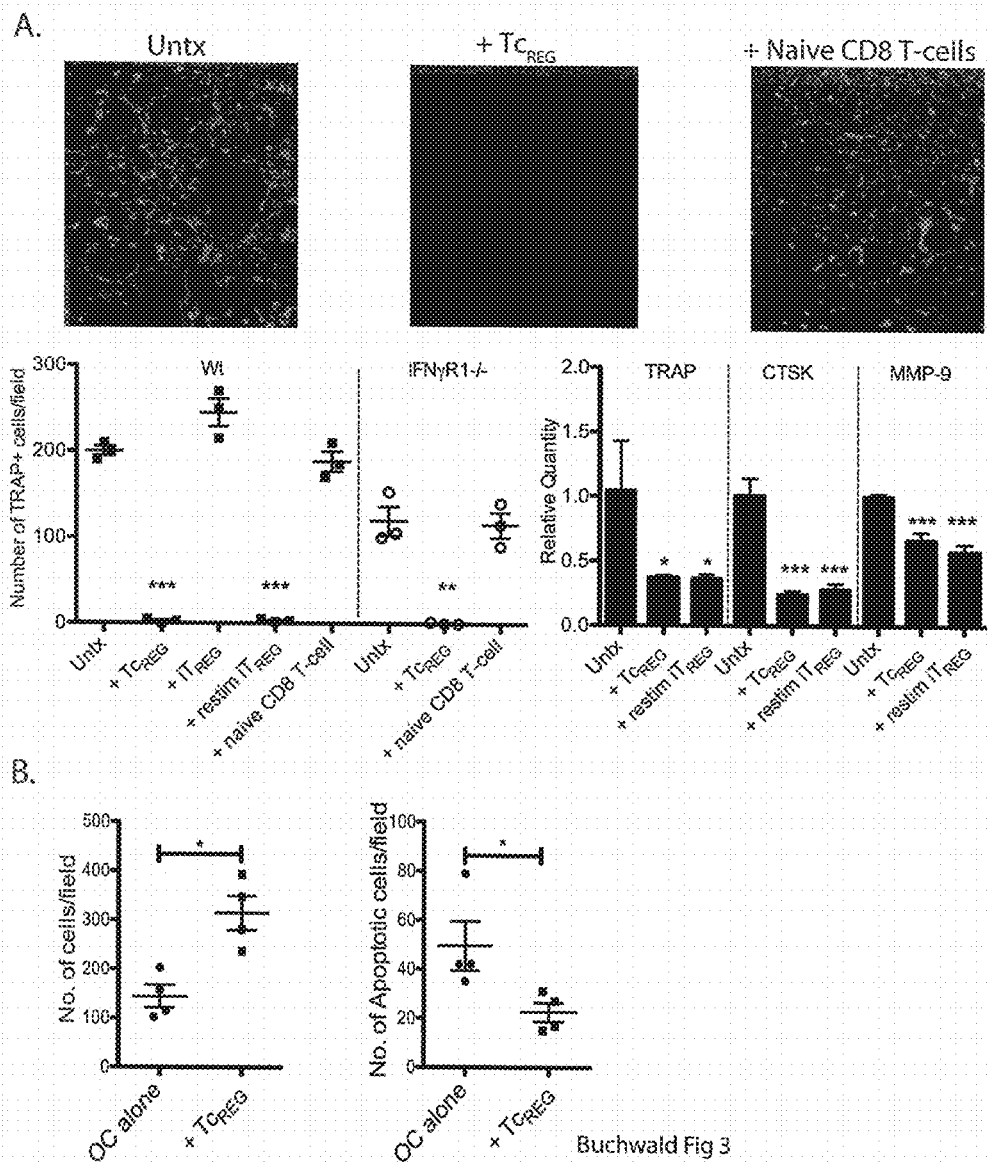
FIGS. 2A and B depict the experimental results that demonstrate that $Tc_{REG}$ can suppress osteoclast differentiation and resorption by mature osteoclasts without affecting their survival.
Figure 4:
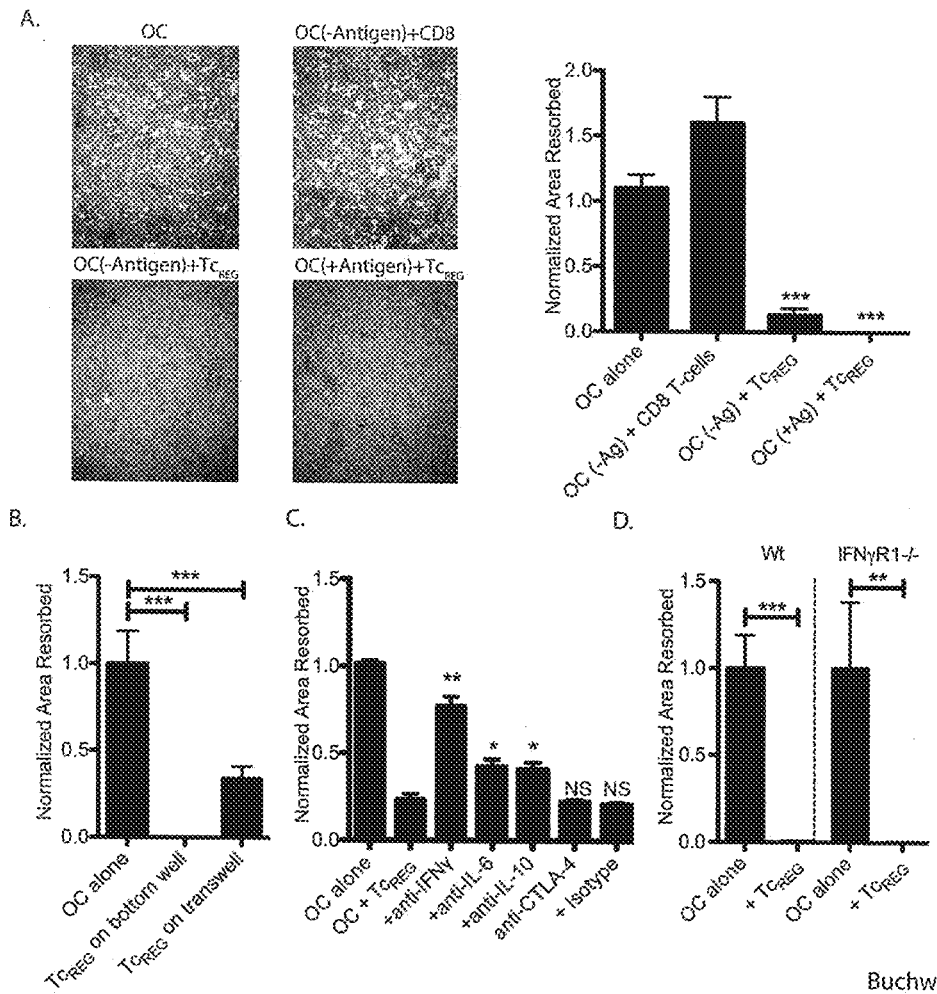
FIG. 4A-D depict the experimental results that demonstrate that suppression is mediated by $Tc_{REG}$ secreted cytokines (IL-2, IL-6, IL-10 and IFN-γ) and does not require direct contact between $Tc_{REG}$ and osteoclasts.

To determine the effect $Tc_{REG}$ secreted cytokines would have on osteoclast activity, experimentation through a number of in vitro assays was undertaken as more fully described in Buchwald, et al., Osteoclast Activated FoxP3+ CD8+ T-cells Suppress Bone Resorption in vitro, *PLoS ONE*, 7:1-12 (2012), the entire disclosure of which is incorporated herein by reference. The results from this experimentation demonstrated that $Tc_{REG}$ secreted cytokines (IL-6, IL-10 and IFN-γ) could suppress osteoclast differentiation and osteoclast resorption. First, it was demonstrated that induction of FoxP3 in CD8 T-cells is antigen dependent; the cytokines are produced by the $Tc_{REG}$ (and not the osteoclasts). Second, as demonstrated in FIG. 1, $Tc_{REG}$ can suppress osteoclast activity on synthetic bone. For example, results demonstrated that $Tc_{REG}$ secreted cytokines could potently and directly suppress resorption by osteoclasts (as demonstrated in FIG. 1). In order to understand how $Tc_{REG}$ suppressed osteoclasts, it was measured to determine if they suppress the birth rate (i.e., differentiation from precursor cells), the death rate (i.e., induce apoptosis or killing) or act merely on mature osteoclasts. As demonstrated in FIG. 2, it was found that $Tc_{REG}$ can suppress osteoclast differentiation and resorption by mature osteoclasts without affecting their survival. It was also demonstrated, as shown in FIG. 3, that $Tc_{REG}$ can directly suppress mature osteoclasts by affecting their cytoskeletal reorganization. This is important because cytoskeletal reorganization is required for osteoclasts to form a sealing zone against the bone to effect breakdown of the bone. Finally, to assess the requirements for suppression, it was measured to determine if direct contact between osteoclasts and $Tc_{REG}$ was required. As demonstrated in FIG. 4, suppression does not require direct contact between the $Tc_{REG}$ and osteoclasts. Rather, the suppression is mediated by $Tc_{REG}$ secreted cytokines (IL-6, IL-10 and IFN-γ), all three of which contribute to the suppression of bone resorption.

Example 2

Ex Vivo Generated $Tc_{REG}$ Tested with RANKL-Administered Mice $Tc_{REG}$ were generated and adoptively transferred using OT-I transgenic T-cells into an OT-I Rag1$^{-/-}$ mouse to determine if $Tc_{REG}$ could suppress bone turnover in vivo under homeostatic conditions. Because the OT-I Rag1$^{-/-}$ mice lack endogenous $Tc_{REG}$ and are not lymphopenic, two potential confounding experimental conditions are eliminated. Forty eight (48) hours after the T-cell transfer, the recipient mice were injected with RANKL. RANKL administration was utilized to increase the sensitivity of the assay by activating bone turnover. The bone turnover was assayed by measuring serum carboxyl-terminal collagen telopeptide crosslinks (CTX) ELISA from blood obtained via sub-mandibular bleeds. T-cells activated with anti-CD3 (αCD3) and αCD28 were used as a control since cells activated in this manner produce significant levels of interferon (IFN)-γ. The untreated and control (IFN)-γ producing T-cell treated mice showed a robust increase in bone resorption in response to 1 mg/kg RANKL. In contrast, as demonstrated in FIG. 5A, mice treated with $Tc_{REG}$ showed an inhibition of osteoclast activity to the same dose of RANKL.

To investigate whether the observed effect; i.e., that OT-I Rag1$^{-/-}$ mice treated with $Tc_{REG}$ showed an inhibition of osteoclast activity, was unique to transgenic $Tc_{REG}$, polyclonal CD8 T-cells were co-cultured with mature osteoclasts in the presence of αCD3 to ligate the TCR of the T-cells. These polyclonal $Tc_{REG}$ were then adoptively transferred into OT-I Rag1$^{-/-}$ recipients. Mice were injected with RANKL and bone turnover was evaluated by serum CTX and μCT. As demonstrated in FIG. 5B, the treated mice had approximately 40% higher bone to total volume (BV/TV) ratios and an increased bone mineral density (BMD) relative to untreated controls. These results indicate that $Tc_{REG}$ are positive modulators of bone density under homeostatic conditions.

Example 3

Ex Vivo Generated $Tc_{REG}$ Tested with Ovariectomized Mice

Figure 5:
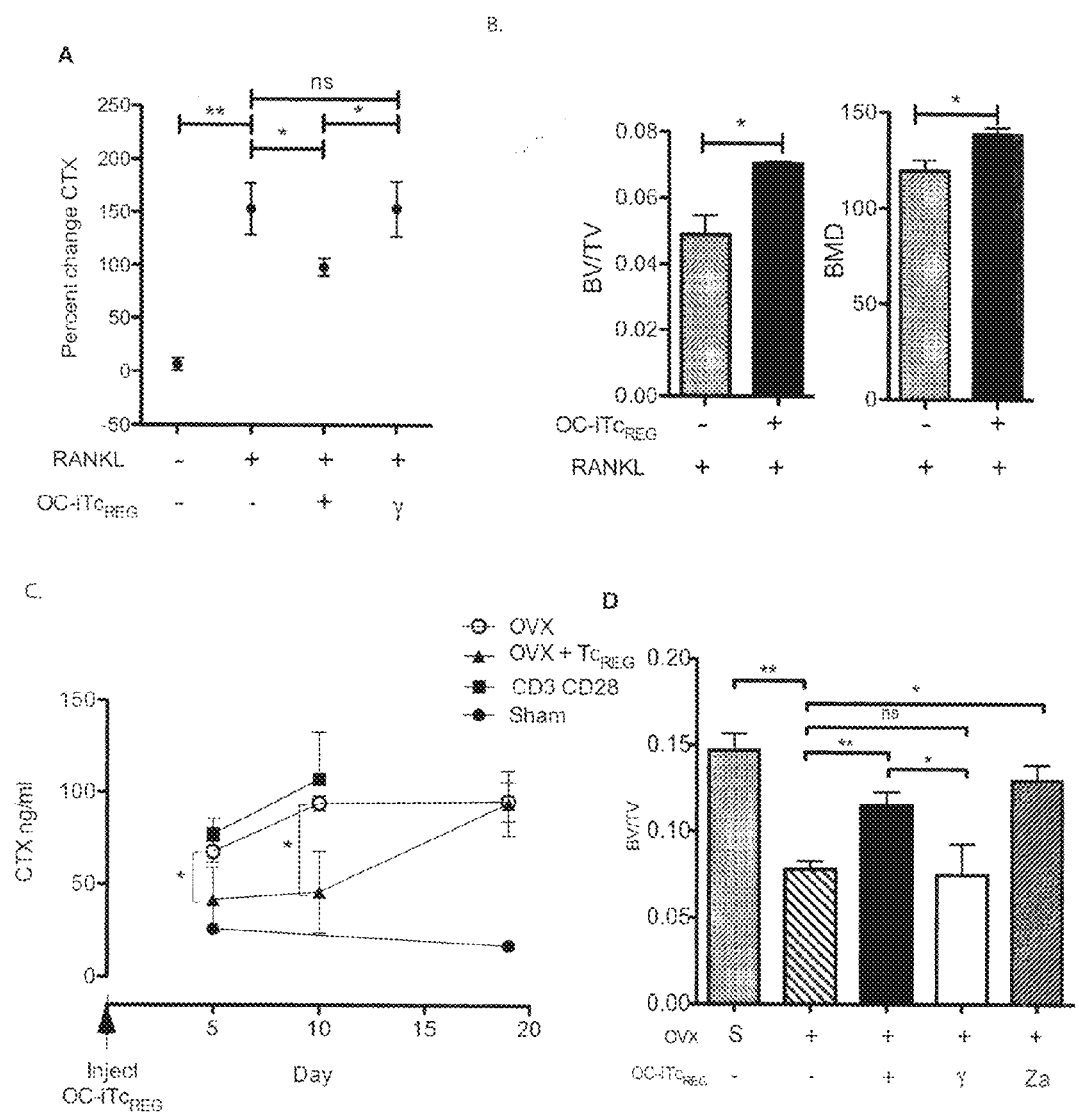
FIG. 5A depicts the experimental results that demonstrate that mice treated with $Tc_{REG}$ showed an inhibition of osteoclast activity to the same dose of RANKL.
FIG. 5B depicts the experimental results that demonstrate that $Tc_{REG}$ are positive modulators of bone density under homeostatic conditions.
FIG. 5C-D depict the experimental results that demonstrate that $Tc_{REG}$ suppress bone loss in ovariectomized mice.

To investigate whether $Tc_{REG}$ could reduce bone turnover when osteoclast activity is instead increased by a pathological condition, the $Tc_{REG}$ in a model of post-menopausal osteoporosis was tested. Experimentation is more fully described in Buchwald, et al., Osteoclast-induced FoxP3 CD8 T-cells Limit Bone Loss in Mice, *Bone*, 56:163-173 (2013), the entire disclosure of which is incorporated herein by reference. A bilateral ovariectomy of 12 to 14 week old mice was performed. Twenty million $Tc_{REG}$ cells were adoptively transferred into ovariectomized (OVX) mice. The adoptive transfer was performed two weeks post-OVX because at this time the osteoclasts were maximally active and the mice already showed significant bone loss. The bone turnover was evaluated by serum CTX using blood samples obtained every five (5) days. As demonstrated in FIG. 5C, while untreated OVX mice or those treated with control T-cells activated by αCD3 plus αCD28 showed an increase in bone resorption from day 5 to day 10 post-T-cell transfer, mice treated with $Tc_{REG}$ showed a plateau in bone turnover during the same interval. Ten (10) days after the transfer, the $Tc_{REG}$ treated mice had an increased BV/TV relative to controls, as seen in FIG. 5D, and the $Tc_{REG}$ were observed in the bone marrow of recipient animals. At twenty (20) days post-transfer, CTX in the $Tc_{REG}$ treated mice had increased control levels, as demonstrated in FIG. 5C, and the $Tc_{REG}$ were no longer present in the bone marrow (data not shown). This suggests an in vivo half-life of approximately 5-7 days and confirms that $Tc_{REG}$ suppress bone loss.

Figure 6:
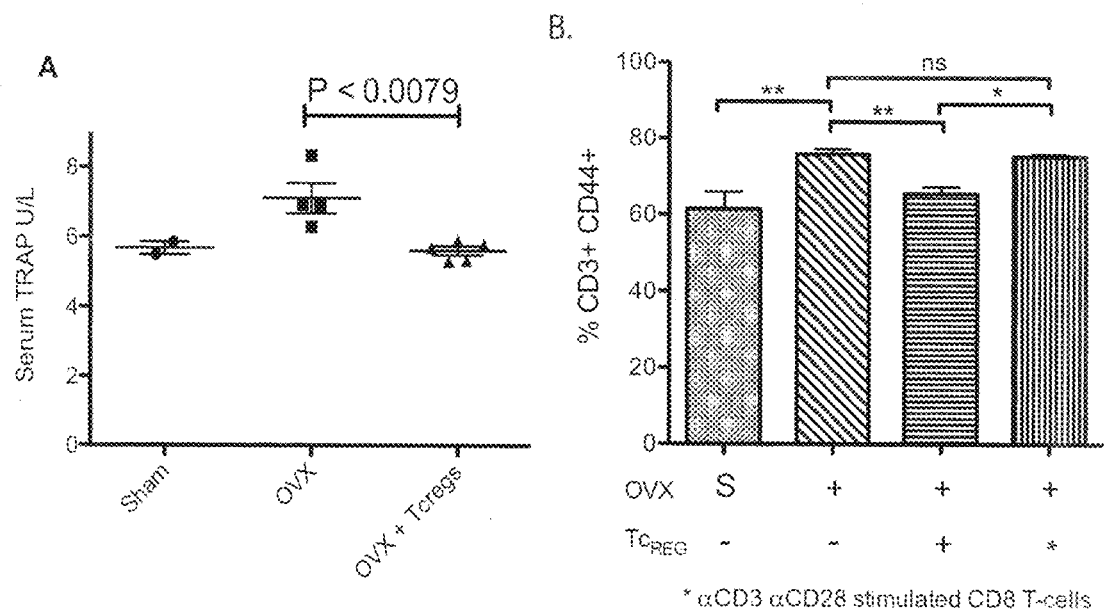
FIG. 6A depicts the experimental results that demonstrate that a decrease in serum TRAP5b (i.e., a measure of osteoclast numbers) was detected in $Tc_{REG}$ treated ovariectomized mice relative to the untreated mice.
FIG. 6B depicts the experimental results that demonstrate that treatment of the ovariectomized mice decreased the numbers of effector T-cells.

Further, it is known that estrogen deficiency also increases the number of activated, pro-inflammatory T-cells (effector T-cells). The cytokines secreted by effector T-cells are an important component of increasing osteoclast activity, leading to bone loss. Consistent with the in vitro studies described previously, a decrease in serum TRAP5b (i.e., a measure of osteoclast numbers) was detected in $Tc_{REG}$ treated ovariectomized mice relative to the untreated mice, as demonstrated in FIG. 6A. The results, depicted in FIG. 6B, show that OVX mice have increased levels of effector T-cells relative to sham surgery (sham surgery is performed to control for effects of anesthesia, inflammation and trauma of incision of skin and for any effects due to handling of the mice)—i.e., treatment of the OVX mice decreased the numbers of effector T-cells. As bisphosphonates, a currently utilized methodology for treating osteoporosis and other bone-loss-based diseases only suppresses osteoclast activity, these results demonstrate that $Tc_{REG}$ could not only suppress osteoclast activity but, by decreasing the number of effector T-cells, could also decrease the pro-inflammatory T-cell response.

Example 4

Endogenous Tc$_{REG}$

To investigate whether endogenous (i.e., natural) Tc$_{REG}$ have regulatory activity similar to the in vitro induced Tc$_{REG}$, a RANKL dose titration was performed on mice sufficient (by weight and CD4$^{-/-}$) and deficient (β2M$^{-/-}$ and TCRα$^{-/-}$) and TCRα$^{-/-}$) in CD8 T-cells. As demonstrated in FIG. 7A-B, the CD8 T-cell deficient mice had elevated bone turnover at higher (>0.5 mg/kg) RANKL doses than the CD8 T-cell sufficient mice. The bone regulatory activity of CD8 T-cells could not be compensated for by the CD4 regulatory T-cells. These results show that there are natural CD8 T-cells that can suppress bone turnover.

Figure 7:
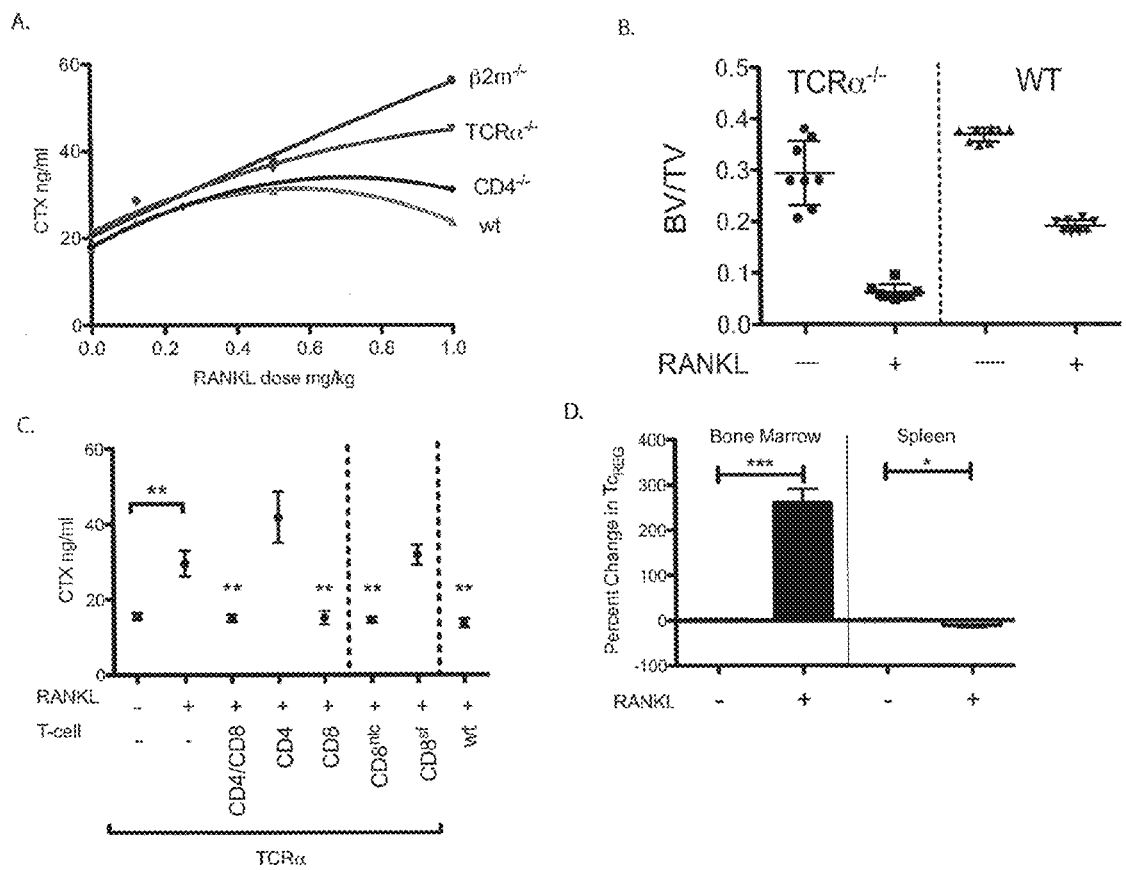
FIG. 7A-B depict the experimental results that demonstrate that the CD8 T-cell deficient mice had elevated bone turnover at higher (>0.5 mg/kg) RANKL doses than the CD8 T-cell sufficient mice.
FIG. 7C depicts the experimental results that demonstrate that CD8 and combined CD4/8 recipients had lower osteoclast activity than the CD4 alone recipients.
FIG. 7D depicts the experimental results that suggest that $Tc_{REG}$ may be induced in the bone in vivo via osteoclast activity.

To address any concerns that different genotypes may respond differently to RANKL, TCRα$^{-/-}$ mice (which lack all αβT-cells) were reconstituted with CD8, CD4, or both CD4 and CD8 T-cells. Following a ten (10) day incubation period to allow the transferred cells to achieve steady state levels in the lymphopenic mice (i.e., homeostatic proliferation) the mice were injected with 1 mg/kg RANKL. The results demonstrated that CD8 and combined CD4/8 recipients had lower osteoclast activity than the CD4 alone recipients, as depicted in FIG. 7C. Further, when the natural Tc$_{REG}$ numbers in RANKL treated and untreated mice were investigated, a large increase in the Tc$_{REG}$ fraction in the bone marrow but not the spleen of the RANKL treated animals was discovered, suggesting that Tc$_{REG}$ may be induced in the bone in vivo via osteoclast activity, as depicted in FIG. 7D.

To determine if FoxP3 expression by the CD8 fraction was required for bone suppressive activity, TCRα$^{-/-}$ mice (mice that lack all αβT-cells) were reconstituted with CD8 T-cells from either normal littermates (CD8$^{n/c}$) of FoxP3 null CD8 T-cells (CD8$^{sf}$) from Scurfy mice. CD8$^{sf}$ refers to CD8 T-cells from a Scurfy mouse that has a non-functional FoxP3 gene. As demonstrated in FIG. 7C, only the FoxP3 sufficient T-cells could suppress bone turnover. These results demonstrate that CD8 T-cells that can functionally produce FoxP3 are required to suppress bone turnover in response to RANKL administration. These results also show that endogenous Tc$_{REG}$, like their in vitro generated counterpart, can suppress osteoclast activity in vivo.

Examples 2 and 3 demonstrate that ex vivo generated osteoclast-induced Tc$_{REG}$ (OC-i Tc$_{REG}$) can suppress bone turnover in vivo. The experiments also demonstrate that osteoclast-induced Tc$_{REG}$ can decrease the number of proinflammatory effector T-cells in the bone marrow in ovariectomized mice. Tc$_{REG}$ not only inhibited mature osteoclasts, but also suppressed osteoclast formation. In fact, Tc$_{REG}$ not only prevented bone loss, but in ovariectomized mice treated with Tc$_{REG}$ restored lost bone. Further, example 4 demonstrates that endogenous Tc$_{REG}$ can also regulate bone resorption.

Example 5

Osteoclasts Induce FoxP3 Using Three Signals

Figure 8:
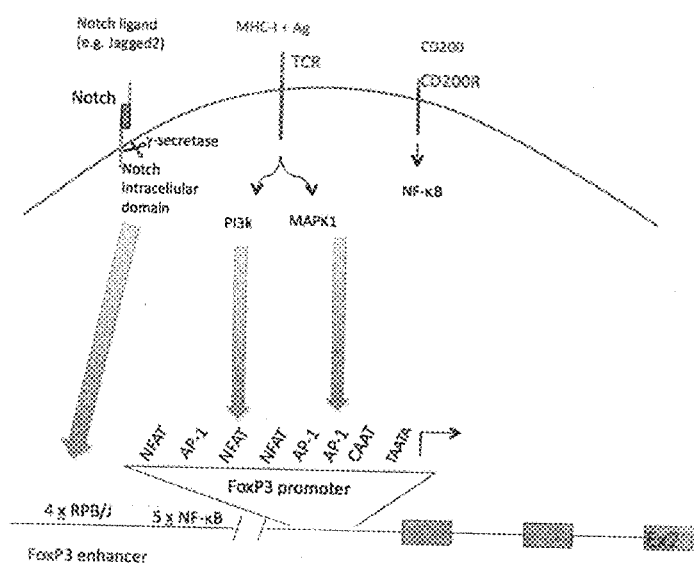
FIG. 8 depicts the three signal pathways used by osteoclasts to induce FoxP3.

It has also been determined, as demonstrated in FIG. 8, that osteoclasts induce Tc$_{REG}$ using three signals. The first is recognition of antigen presented by osteoclasts on major histocompatibility protein class I (MHC-I) by T-cell receptor (TCR). In the T-cell, binding of TCR initiates signaling that stimulates PI3 kinase to release calcium to activate the transcriptional factor NFAT, which directly binds to FoxP3 promoter. MHC-I bound TCR also initiates mitogen activated protein kinase 1 (MAPK1), which activates the transcription factor AP-1, that also binds to FoxP3 promoter. Second, osteoclasts signal via CD200 on osteoclast that engages CD200R on T-cells. CD200R activates the transcription factor NF-κB, which also binds to five sites in the FoxP3 enhancer region. Finally, Notch ligand on osteoclasts engages Notch (receptor), which causes the cleavage of Notch by gamma secretase complex to release the Notch intracellular domain (NICD). NICD associates with RBP/j and also binds to the FoxP3 enhancer. All three signals are needed and are sufficient to induce FoxP3 in CD8 T-cells.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

The invention claimed is:

1. A method for reducing bone loss in a patient, the method comprising:
    generating osteoclasts from ex vivo blood of said patient by culturing blood mononuclear cells with M-CSF and RANKL;
    generating T-cells from said ex vivo blood;
    generating ex vivo said patient, FoxP3+CD8 T-cells (Tc$_{REG}$) by co-culturing said T-cells and said osteoclasts in the presence of αCD3; and
    introducing said (Tc$_{REG}$) to said patient.

* * * * *